US006995245B2

(12) United States Patent
Pool

(10) Patent No.: US 6,995,245 B2
(45) Date of Patent: Feb. 7, 2006

(54) FORMATION OF NOVEL ERYTHROPOIETIN CONJUGATES USING TRANSGLUTAMINASE

(75) Inventor: Chadler Pool, Phoenixville, PA (US)

(73) Assignee: Centocor, Inc., Malvern, PA (US)

( * ) Notice: Subject to any disclaimer, the term of this patent is extended or adjusted under 35 U.S.C. 154(b) by 5 days.

(21) Appl. No.: 10/854,854

(22) Filed: May 27, 2004

(65) Prior Publication Data

US 2004/0266690 A1 Dec. 30, 2004

Related U.S. Application Data

(60) Provisional application No. 60/475,074, filed on May 30, 2003.

(51) Int. Cl.
*A61K 38/18* (2006.01)
*C07K 14/00* (2006.01)
(52) U.S. Cl. .................. 530/399; 530/300; 514/2; 435/68.1
(58) Field of Classification Search ............ 514/2
See application file for complete search history.

(56) References Cited

U.S. PATENT DOCUMENTS

| 4,806,524 | A | | 2/1989 | Kawaguchi et al. |
| 4,904,584 | A | | 2/1990 | Shaw |
| 5,438,040 | A | * | 8/1995 | Ekwuribe ............... 514/3 |
| 6,010,871 | A | | 1/2000 | Takahara et al. |
| 6,077,939 | A | | 6/2000 | Wei et al. |
| 6,322,996 | B1 | | 11/2001 | Haruya et al. |
| 6,331,422 | B1 | | 12/2001 | Hubbell et al. |
| 6,340,742 | B1 | | 1/2002 | Burg et al. |
| 6,465,694 | B1 | * | 10/2002 | Baudys et al. .......... 568/494 |
| 6,583,272 | B1 | | 6/2003 | Bailon |
| 2004/0082765 | A1 | | 4/2004 | Nakamura et al. |

FOREIGN PATENT DOCUMENTS

| EP | 0539167 A2 | 10/1992 |
| WO | WO 90/12874 A2 | 11/1990 |
| WO | WO 94/28024 A1 | 12/1994 |
| WO | WO 00/43492 A2 | 7/2000 |
| WO | WO 01/02017 A2 | 1/2001 |

OTHER PUBLICATIONS

Sato, H. Advanced Drug Delivery Reviews 54: 487-504 (2002).*
Groenen et al, "The carboxy-terminal lysine of xB-crystallin is an amine-donor substrate for tissue transglutaminase," *J. Biochem*, 1992, pp 671-674, vol. 205.
Sata et al, "Site-Specific Modification of Interleukin-2 by the Combined Use of Genetic Engineering Techniques and Transglutaminase," *BIOCHEMISTRY*, 1996, pp 13072-13080, vol. 35.
Gorman et al, "Structural Features of Glutamine Substrates for Human Plasma Factor XIIIa (Activated Blood Coagulation Factor XIII), " *The Journal of Biological Chemistry*, 1980, pp 419-427, vol. 255, No. 2.
Dale et al, "Stimulated platelets use serotonin to enhance their retention of procoagulant proteins on the cell surface," *Letters to Nature*, 2002, pp 175-179, vol. 415, Macmillan Magazines Ltd.
Grootjans et al, "Substrate Requirements for Transglutaminases," *The Journal of Biological Chemistry*, 1995, pp 22855-22858, vol. 270, No> 39, The American Society for Biochemistry and Molecular Biology, Inc.
Gorman et al, "Structural Features of Glutamine Substrates for Transglutaminases," *The Journal of Biological Chemistry*, 1981, pp 2712-2715, vol. 256, No. 6, U.S.A.
Fisher, "Erythropoietin: Physiology and Pharmacology Update," *Exp. Biol Med.*, 2003, pp 1-14, 228 (1).

* cited by examiner

*Primary Examiner*—Jon Weber
*Assistant Examiner*—Anand Desai
(74) *Attorney, Agent, or Firm*—Guy Kevin Townsend

(57) ABSTRACT

The invention provides biologically active erythropoietin (EPO) conjugate compositions wherein a transglutaminase reaction is employed to covalently and site specifically conjugate the EPO molecule to a non-antigenic hydrophilic polymer that can also be covalently linked to an organic molecule either of which modification increases the circulating serum half-life of the composition.

32 Claims, 13 Drawing Sheets

```
APPRLICDSR VLERYLLEAK EAENITTGCA EHCSLNENIT VPDTKVNFYA WKRMEVGQQA        60

VEVWQGLALL SEAVLRGQAL LVNSSQPWEP LQLHVDKAVS GLRSLTTLLR ALGAQKEAIS       120

PPDAASAAPL RTITADTFRK LFRVYSNFLR GKLKLYTGEA CRTGDR                     166
```

FIG. 1

FORMATION OF NOVEL ERYTHROPOIETIN CONJUGATES USING TRANSGLUTAMINASE

CROSS REFERENCE TO RELATED APPLICATION

This application is a non-provisional application filed under 37 CFR 1.53(b)(1), claiming priority under 35 USC 119(e) to provisional application No. 60/475,074 filed May 30, 2003, the contents of which are incorporated herein by reference.

FIELD OF THE INVENTION

The present invention relates to novel formulations of erythropoietin prepared using an enzymatic method of attaching groups to the structure or altering the bioactivity through mutations of the primary sequence. In particular, the invention relates to erythropoietin conjugate compounds having altered physiochemical and pharmacokinetic properties.

BACKGROUND OF THE INVENTION

Erythropoietin (EPO) is a naturally formed glycoprotein which functions as a colony stimulating factor and serves as the principal factor involved in the regulation of red blood cell synthesis. Erythropoietin acts by stimulating precursor cells in bone marrow causing them to divide and differentiate into mature red blood cells. This process is tightly controlled in the body such that the destruction or removal of red cells from the circulation is matched by the rate of new cell formation. Naturally occurring EPO is a glycoprotein produced in the kidney (Jacobs, et al. Nature 313 (6005), 806–810 (1985).

Erythropoietin has been manufactured using recombinant DNA technology through the cloning of the EPO gene and expression in Chinese hamster ovary cells (Lin, U.S. Pat. No. 5,618,698). The recombinantly produced EPO has been available for some time as an effective therapeutic agent in the treatment of various forms of anemia, including anemia associated with chronic renal failure, zidovidine treated HIV infected patients, and cancer patients on myelosuppressive chemotherapy. The glycoprotein is administered parenterally, either as an intravenous (IV) or subcutaneous (SC) injection in conventional buffered aqueous solutions which contain human serum albumin (HSA) as a carrier. Such formulations are marketed in the United States under the trade names EPOGEN® and PROCRIT®. These products contain erythropoietin in 1 ml single dose, preservative-free or 2 ml multidose preserved vials.

While these formulations have been proven to be highly successful, certain disadvantages are associated with the products. Presently, the period of bioactivity of protein therapeutics such as erythropoietin is limited by short plasma half-lives and the susceptibility to protease degradation. The short half-life of therapeutic proteins such as EPO, four hours, necessitates frequent administration for maximum clinical efficacy. This is disadvantageous for the treatment of chronic conditions and can result in poor patient compliance, and therefore less than optimal outcome. Accordingly, attempts have been made to increase the plasma half-life of EPO.

In recent years, non-antigenic water-soluble polymers, such as polyethylene glycol (PEG) have been used for the covalent modification of polypeptides of therapeutic and diagnostic importance. For example, covalent attachment of PEG to therapeutic polypeptides such as the interleukins (Knauf, M. J. et al., *J. Biol. Chem.* 1988, 263, 15, 064; Tsutsumi, Y. et al., *J. Controlled Release* 1995, 33, 447), interferons (Kita, Y. et al., *Drug Des Delivery* 1990, 6, 157), catalase (Abuchowski, A. et al., *J. Biol. Chem.* 1977, 252, 3, 582), superoxide dismutase (Beauchamp, C. O. et al., *Anal Biochem.* 1983, 131, 25), and adenosine deaminase (Chen, R. et al, *Biochim, Biophys. Acta* 1981, 660, 293), has been reported to extend their half-life in vivo, and/or reduce their immunogenicity and antigenicity.

Derivatized PEG compounds have been previously disclosed (U.S. Pat. No. 5,438,040, Aug. 1, 1995, Conjugation-Stabilized Polypeptide Compositions, Therapeutic Delivery and Diagnostic Formulations Comprising Same, and Method of Making and Using the Same, N. N. Ekwuribe). This approach to post-translational derivatization has also been applied to EPO. For example, WO 94/28024 discloses carbohydrate modified polymer conjugates with erythropoietin activity wherein the PEG is linked via an oxidized carbohydrate. U.S. Pat. No. 4,904,584 discloses polyalkylene oxide conjugation of lysine-depleted polypeptide variants, including EPO. WO 90/12874 describes the preparation of a monomethoxy-PEG-EPO (mPEG-EPO) in which the EPO contains a cysteine residue introduced by genetic engineering to which the specific PEG reagent is covalently attached. Other PEG-EPO compositions are disclosed in EP 605693, U.S. Pat. No. 6,077,939, WO 01/02017 and EP 539167.

Applicant's co-pending application U.S. Ser. No. 09/431,861 discloses the modification of antibodies and antibody fragments with PEG and demonstrates that PEG can increase circulating half-life in mice and primates. Derivatized PEG was used for modification of the Fab fragment of the antibody c7E3. Circulating half-life is increased in direct proportion to the molecular weight of the PEG. As the molecular weight of PEG increases, the ability of the compound to inhibit ADP-induced platelet aggregation in vitro is decreased, while the binding to purified GPIIb/IIIa, as measured by BIAcore, is unaffected. The addition of a fatty acid or a lipid to the PEG ($PEG_{3.4K}$-DSPE [disteroylphosphatidylethanolamine]) yielded a greater circulating half-life than did $PEG_{5K}$. While there is a decrease in the in vitro activity of c7E3 Fab'$(PEG_{5k})_2$ relative to c7E3 Fab, the activity of c7E3 Fab'-$(PEG_{3.4K}$-DSPE$)_2$ is equivalent to c7E3 Fab.

Applicant's other co-pending application U.S. Ser. No. 60/377,946 discloses methods for modifying EPO in which the EPO is covalently conjugated to a non-antigenic hydrophilic polymer covalently linked to an organic molecule that increases the circulating serum half-life of the composition more than what can be achieved by addition of a hydrophilic polymer alone. The methods include the step of reacting a protein or glycoprotein having erythropoietic activity with a substantially non-antigenic functionalized hydrophilic polymer having a linking group for attaching the polymer to the glycoprotein. Preparation methods include reacting EPO with an activated form of a polyalkylene oxide that will react with a functional group on EPO. This includes activated polyalkylene oxides such as active esters, hydrazide, hydrazine, semicarbazide, thiosemicarbazide maleimide or haloacetyl polyalkylene oxide.

An often limiting aspect of many methods of modifying proteins by conjugation to PEG ("PEGylation") using purely chemical methods, is the indiscriminate and often incomplete reaction with amine groups which may occur on accessible lysine residues and/or the N-terminal amine of the protein. Other chemical methods require oxidation of the carbohydrate groups as part of the modification strategy likewise leading to incomplete or inconsistent reactions and undefined product compositions. Thus, considering the present options available, a method for modifying EPO in a mild, site-specific manner would be advantageous.

Transglutaminases (TGases) [EC2.3.2.13; protein-glutamine:gamma-glutamyltransferase] are a family of proteins that catalyze the calcium-dependent acyl addition to a primary amine wherein the gamma-carboxamide group of peptide-bound glutamine residue is the acyl donor and the primary amine is the acyl acceptor and amine donor. In nature, TGases crosslink proteins by catalyzing the formation of amide bonds between lysine and glutamine residues on opposing proteins. A well-known example is fibrin cross-linking by the TGase factor XIIIa. This bond is stable and resistant to proteases and thus, TGases are generally used to link structural components of cells. In addition to the above mentioned plasma form, TGases are found in tissues such as liver, skin, and extracellular fluids (Greenberg, C. Set al. *FASEB J.* 1991, 5, 3071–3077). Prokaryotic forms of TGase are also known (Ando, H. et al. Agric. Biol. Chem 53 (10), 2613–2617, 1989; Washizu, K. et al. Biosci. Biotech. Biochem 58(1), 82–87, 1994). The specificity of TGases is quite pronounced with usually only one, or in some cases two, glutamine residues per protein serving as amine acceptors. TGases from various mammalian tissues and species have been extensively studied (Folk, J. E. and Chung, S. I. *Adv. Enzym. Molec. Biol.* 1973, 38, 109–191; Folk, J. E. and Finlayson, *J. S. Adv. Protein Chem.* 1977, 31, 1–133; Folk, J. E & Cole, P. W. *Biochim Biophys. Acta* 1966, 122, 244–264; Folk, J. E.; Chung, S. I. *Methods in Enzymology* 1985, 113, 358–375;). Thus, TGases could and have been employed to site-specifically modify glutamine residues on some proteins (U.S. Pat. No. 6,010,871; U.S. Pat. No. 6,331,422; U.S. Pat. No. 6,322,996).

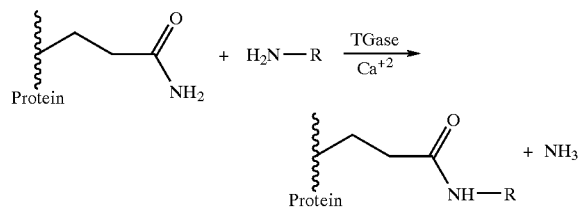

Despite numerous studies, few details about the determinants of TGase specificity have been elucidated. TGases differ in substrate specificities, and when choosing residues as acyl donors or acceptors, the preference for specific sequence motifs as containing or neighboring the substrate residue has not generally been identified for individual enzymes (Gorman, J. J.; Folk, J. E. *J. Biol. Chem.* 1981, 256, 2712–2715; Gorman, J. J.; Folk, J. E. *J. Biol. Chem.* 1980, 255, 419–427). The only definitive rule is that a glutamine residue must be positioned at least three residues from the N-terminus to serve as a substrate for any TGase. In general, glutamine repeats have been shown to enhance the acceptor properties of each glutamine residue in the repeat, and the accessibility of glutamine residues has also been shown to be important in determining their ability to function as TGase substrates (Kahlem, P. et al. Proc. Natl. Acad. Sci. USA 1996, 93, 14580–14585).

Although the site-specific nature of TGase modifications has been known since the 1960s, and industrial uses in the food stabilization are practiced, only recently have uses in therapeutic protein modification begun to be explored. The use of TGases to attach 5 kilodalton or larger polymers containing aliphatic amino groups to protein bound glutamine residues was recently disclosed by Sato, et al in U.S. Pat. No. 6,322,996. This patent also discloses the methods of engineering proteins to contain added N-terminal or C-terminal peptides which are known to be TGase substrates for the purpose of subsequent attachment of large polymers using TGase catalysis. The PEGylation of IL-2 has been accomplished using these methods (Sato, H.; Ikeda, M.; Suzuki, K.; Hirayama, K. *Biochemistry* 1996, 35, 13072–13080), the cross-linking of IL-2 to various other proteins using bacterial TGase was also demonstrated (Takahara, Y. et al. U.S. Pat. No. 6,010,871), and use of factor XIIIa in the production of a modified fibrin matrix for tissue engineering (U.S. Pat. No. 6,331,422).

The modification or addition of motifs to a naturally occurring molecule carries multiple risks that are well known to those practicing the art of genetic engineering for the purposes of providing manufacturing methods for therapeutic proteins. The most obvious of these effects is the loss or partial loss of biological activity. In other cases, the expression level from constructed expression vectors is unacceptably low when incorporated into mammalian cell lines. The alternate approach of coupling or fusion of a known substrate sequence from a naturally occurring protein substrate may create an antigenic epitope and cause unwanted immune reactions in the subject which ultimately limit the long term efficacy of the therapeutic protein. Furthermore, the modification of proteins using chemical methods that attack the most reactive functional group, lysine, also changes the isoelectric point of the protein and the pKa. Therefore, when the objective is to provide safe and economically produced products, it is important to understand these limitations. The conversion of the amide group of glutamine to an alkylated amine does not change the isoelectric point or charge of that glutamine. Thus, use of an enzymatic process that creates a stable covalent bond while not modifying the electrical charge of the protein would be desirable. Heretofore, EPO has not been considered a natural TGase substrate nor has the re-engineering of the molecule in order to create or eliminate TGase substrate sites in EPO been described.

SUMMARY OF THE INVENTION

The invention provides biologically active EPO conjugate compositions wherein EPO is erythropoietin or its pharmaceutical acceptable derivatives having biological properties of causing bone marrow cells to increase production of reticulocytes and red blood cells, wherein a transglutaminase reaction is employed to covalently and site specifically conjugate the EPO molecule to a non-antigenic hydrophilic polymer that can also be covalently linked to an organic molecule either of which modification increases the circulating serum half-life of the composition.

More particularly, one embodiment of the invention thus relates to EPO derivatives described by the formula $$EPO\text{-}[Gln\text{-}A\text{-}X\text{-}(M)_n]_y \quad (I)$$

where EPO is erythropoietin or its pharmaceutical acceptable derivatives having biological properties of causing bone marrow cells to increase production of reticulocytes and red blood cells; Gln is a glutamine residue selected from one or more glutamine residues within the primary sequence of EPO; y is an integer from 1 to 7 indicating the number of modified glutamine residues; A is an amine donor moiety or a hydroxyl group, X is an optional hydrophilic polymer moiety; M is an optional organic molecule (including peptides and proteins) that increases the circulating half-life of the construct; and n is an integer from 0 to 15. The moieties X and M may be modified as needed to include groups designed to provide the proper functionality for coupling or valency.

The organic molecule, M, is optional, and is covalently attached to the hydrophilic polymer. M is selected from an organic moiety that is capable of increasing the in vivo half-life of the resulting construct and include fatty acids, dicarboxylic acids, monoesters or monoamides of dicarboxylic acids, lipids containing saturated fatty acids, lipids containing unsaturated fatty acids, lipids containing mixtures of saturated and unsaturated fatty acids, simple carbohydrates, complex carbohydrates, carbocycles (such as steroids), heterocycles (such as alkaloids), amino acid chains, proteins, enzymes, enzyme cofactors, or vitamins.

The hydrophilic polymer is preferably a polyalkylene oxide such as polyethylene glycol.

Another embodiment of the invention relates to EPO derivatives described by the formula

$$\text{EPO-}[\text{Lys-Gln-Z-X-}(M)_n]_y \quad \text{(II)}$$

where EPO is erythropoietin or its pharmaceutical acceptable derivatives having biological properties of causing bone marrow cells to increase production of reticulocytes and red blood cells; Lys is a lysine residue selected from one or more lysine residues within the primary sequence of EPO; y is an integer from 1 to 8 indicating the number of modified lysine residues; Gln is a glutamine residue; Z is peptide or protein containing the Gln residue that is capable of acting as transglutaminase amine acceptor, X is an optional hydrophilic polymer; M is an optional organic molecule (including peptides and proteins) that increases the circulating half-life of the construct; N is an integer from 0 to 15. The moieties X and M may be modified as needed to include groups designed to provide the proper functionality for coupling or valency.

The present invention also provides methods of preparing the conjugates. The methods include the step of using a TGase to catalyze the acyl transfer of an amino group donor or an alkylamine-conjugate to one or more specific glutamine residues in aglycosylated or glycosylated EPO or a glycoprotein having erythropoietic activity having a glutamine residue. The methods also include the step of using TGase to catalyze the acyl transfer of an amino group donor on EPO to one or more glutamine residues in a peptide, protein, or other polymer.

Included in the present invention is the disclosure of EPO as a TGase substrate. Therefore, also included in this invention is a method of altering an EPO molecule by recombinant or chemical means to mutate, add or modify any glutamine or lysine residues or any other residues, to enable or to improve the ability of the EPO molecule to act as a TGase substrate properties thereby allowing the conjugation of the EPO molecule to a hydrophilic polymer or other organic moiety containing an amine donor or amine acceptor moiety. Since TGase substrate properties can be involved in the biological activity of proteins, improving or diminishing the TGase substrate properties of an EPO molecule through recombinant or chemical means is also included in this invention. Thus, in accordance with the invention, the EPO molecule can be modified to increase the circulation half life or otherwise improve the biological activity of mammalian erythropoietin or any conjugate or mutant erythropoietic protein.

The invention also provides methods of treating anemia or other conditions associated with reduced endogenous erythropoietin or erythropoiesis or conditions under which an increase in red cells is desired. In this aspect of the invention, treatment includes administering an effective amount of the conjugates described herein to mammals requiring such therapy. As a result of the present invention, conjugates having substantially prolonged erythropoietic activity in vivo are provided.

The techniques disclosed herein have the advantage of providing EPO molecules with an increased circulating half-life and improved erythropoietic potency. Further, the modified EPO molecules of the invention have an advantage in that the conjugation and/or mutations are well controlled leading to end products that are substantially well defined and characterized.

BRIEF DESCRIPTION OF THE DRAWINGS

FIG. 1 shows the amino acid sequence of the mature chain of human erythropoietin with the glutamine residues in boxes.

DETAILED DESCRIPTION

Figure 2:
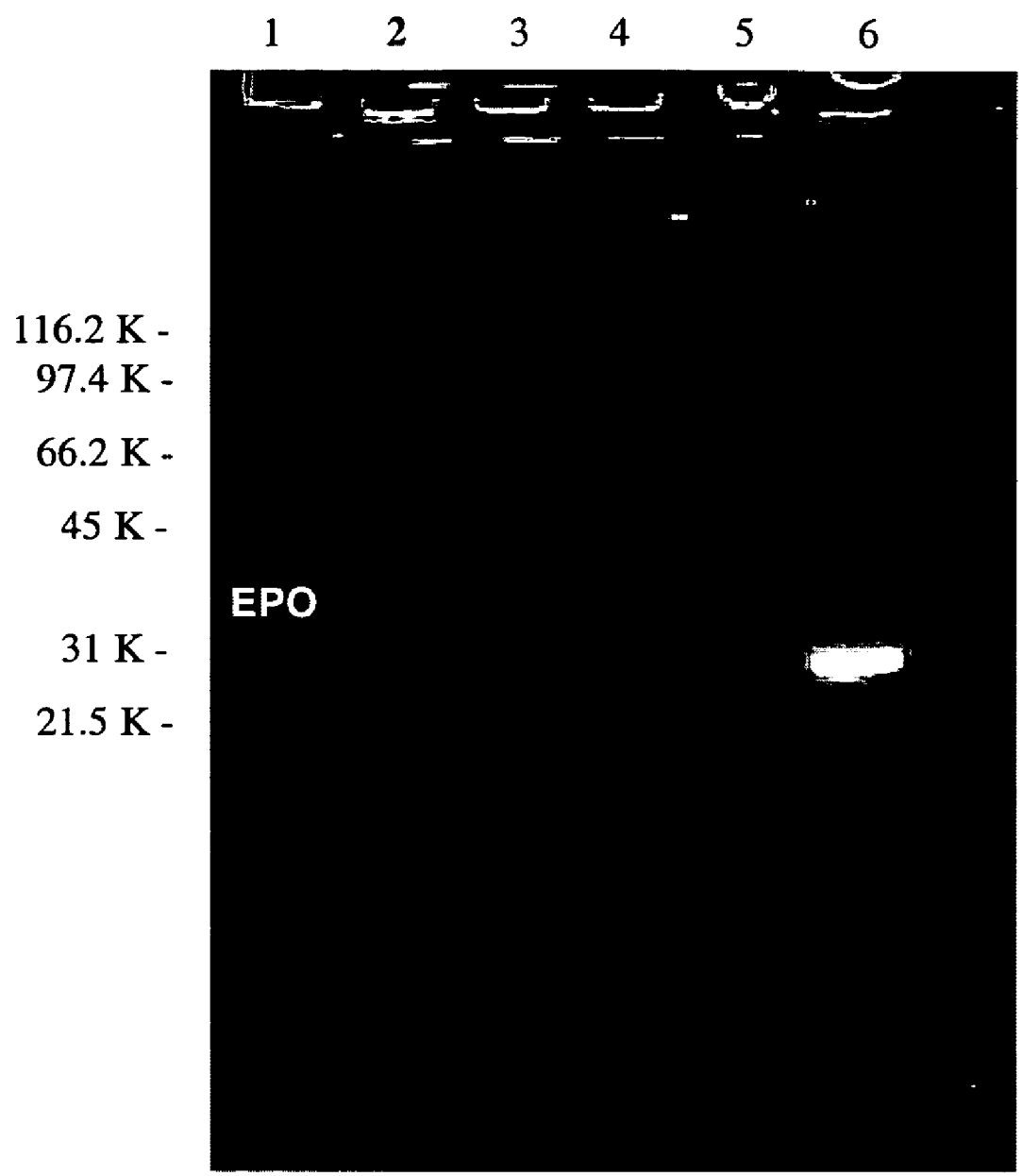
FIG. 2 is an image of an SDS-PAGE gel in which a fluorescently-labeled TGase substrate, dansyl cadaverine (DC), was incubated with proteins in the presence or absence of TGase. The label is visualized using UV exposure: Lane 1=molecular weight markers. Lane 2=EPO+DC+TGase. Lanes 3 and 4=EPO+DC; Lane 5=EPO standard; and lane 6=b-casein+DC+TGase. b-casein is a known substrate for TGase and was used as a positive control. The fluorescent 35 K band in lane 2 corresponds to EPO with one or more DC moieties attached. The higher molecular weight bands in lane 2 likely correspond to EPO dimers and trimers. The same gel was silver stained to identify the molecular weight markers and other, non-fluorescent bands.

EPO is primarily produced in the kidneys and functions through binding to receptor dimers on precursor cells leading to differentiation to erythrocytes and subsequent proliferation (Livnah, O. et al. *Science* 1999, 283, 987–990). The primary sequence of EPO has 7 glutamine residues. The assembled NCBI file, P01588, notes glutamines at positions; 85, 86, 92, 105, 113, 119, and 142 of the precursor protein corresponding to; 58, 59, 65, 78, 86, 92, and 115 of the mature chain. These are shown in FIG. 1.

EPO binds to the receptors through two binding surfaces, one of which has a higher affinity for the receptor than the other. The crystal structure of EPO has been solved (Syed, et al. Nature 395 (6701), 511–516 (1998); Cheetham, J. C. et al. Human Erythropoietin, NMR minimized average structure. 8 Sep. 1998. Protein data base ID 1BUY). The crystal structure of EPO binding to its receptors has also been described (see Stroud, R. M. and Reid, S. W., Erythropoietin complexed with extracellular domains of erythropoietin receptor. Protein data base ID 1CN4). Within the complex, four of the eight lysine residues on EPO make direct contacts with the receptors while of the 7 glutamine residues, all but one are solvent accessible and only Gln78 shows any possible interaction with the receptors. From these observations, it is apparent that the glutamine residues on EPO offer significant potential for attachment of PEG or other polymers without interfering with receptor binding, while indiscriminate modification of lysine residues is almost certain to interfere with binding to some extent.

Although several of the lysine residues present on EPO are involved in receptor binding, others would offer significant potential for attachment of PEGs or other polymers if they could be modified specifically. Since TGases are extremely selective regarding lysines on proteins that can serve as amine-donor substrate sites, the possibility exists for using TGases to attach polymers to these lysine residues should they be selectively targeted by TGases.

Since TGases are present in many mammalian fluids and tissues, the discovery that EPO is a TGase substrate indicates that, as such, transglutaminase-catalyzed reactions in vivo could impact the bioavailability and distribution of any therapeutic protein containing sequences from mammalian erythropoietin that include glutamine and/or lysine residues. Thus, it follows that eliminating, masking, or modifying these residues to decrease or eliminate their inherent TGase substrate properties could significantly alter the biological properties of such a biopharmaceutical agent and enhance the efficacy of any such erythropoietic protein. Such modifications are made by mutating said glutamine and/or lysine residues to any of the other 19 naturally occurring amino acids, chemically modifying said lysine and/or glutamine residues, or by attaching small acyl-donor or amine-donor substrates to these sites using TGases thereby eliminating them as TGase substrates. Also, some residues have been suggested to improve or diminish the substrate properties of lysine or glutamine residues contained within peptides or proteins. Thus, the mutation, addition, or chemical modification of other residues within the sequence of an erythropoietic protein could improve or diminish the substrate properties of lysine of glutamine residues contained within the primary amino acid sequence of the protein. In a recent paper (Dale, et al. Nature 415 (10), 175–179 (2002)) the authors show that serotonin is a TGase substrate and becomes bound to activated platelets through TGase-catalyzed crosslinking to surface proteins. The TGases factor XII and tissue transglutaminase were identified on the surface of activated platelets. The crosslinking of serotonin to the platelet surface augments the retention of procoagulation proteins on the cell surface. This study shows that extracellular TGases can crosslink proteins containing TGase substrate sites to cell surfaces and that this activity can potentially facilitate the binding of a protein with its receptor. This suggests that the TGase substrate properties exhibited by EPO could be directly involved in the erythropoietic potency of the protein if TGases are involved in binding the protein to erythroid progenitor cells or other targeted cell lines.

EPO

The starting material for modification to a bioactive form of EPO is preferably erythropoietin or its derivatives having the biological properties of causing bone marrow cells to increase production of reticulocytes and red blood cells. The EPO glycoprotein may be obtained from natural sources or produced recombinantly using known procedures as disclosed in U.S. Pat. Nos. 4,703,008; 5,441,868; 5,547,933; 5,618,698 and 5,621,080 hereby incorporated by reference. Nonglycosylated forms or hyperglycosylated forms of erythropoietin protein with the desired biological activity may also be used. Methods of producing hyperglycosylated EPO are taught in WO0249673 and EP640619.

Transglutaminases

Any of the enzymes catalyzing the acyl transfer from glutamine to an acceptor are suitable for use in the present invention. Transglutaminase, derived from guinea pig liver, is particularly suitable, and readily available through commercial sources e.g. Sigma Chemical Co., ICN Chemicals, and the like. TGases of microbial origin may also be used, for example, the calcium independent transglutaminase of *Streptoverticillium* sp. or from *Streptoverticillium mobaraense* (Ando et al. Agric. Biol. Chem., 53(10), 2613–17, 1989).

Acyl Acceptors/Amine Donors

TGases have a broad specificity for primary amine donors which may be either primary amine containing compounds, or peptide- or protein bound epsilon-amino groups of lysine. Amine-donor substrates for TGases include: ammonia, hydroxylamine, methylamine, ethanolamine, phenylethylamine, histamine, spermine, spermidine, cadaverine, putrescine, protein- or peptide-bound lysine groups, amine amides such as glycinamide but not L-tyrosinamide. N-(5-aminopentanyl)-5-dimethylamino-1-naphthalene-sulfonamide (dansylcadaverine) is a useful substrate for testing protein substrates due to its fluorescent nature and ability to act as an excellent amine-donor (see Folk and Chung, 1973 supra).

Water can also act as a nucleophile here, resulting in the conversion of glutamine to glutamic acid in which case the moiety A in formula I above is a hydroxyl moiety.

Aminosaccharides, see for example WO0179474, and aminoalkylsaccharides, in JP2000300287, have also been shown to be suitable amine donors for transglutaminase-catalyzed attachment to proteins. Aminosaccharides are any monosaccharide, oligosaccharide or polysaccharide containing a primary amino group and any monosaccharide, oligosaccharide or polysaccharide prepared by means of reductive amination of a monosaccharide, oligosaccharide or polysaccharide in order to introduce an amine group. An example of an advantageous aminosaccharide is aminosorbitol.

Thus, any of the above mentioned or related compounds may act as the amine donor and further may themselves be modified in order that the trans-acylation reaction catalyzed by the TGase will effectively conjugate the group desired to be added to the EPO structure at said glutamine residue. Particularly preferred molecules representing the A moiety of formula I are: cadaverin, putrescine, 1,5-diaminopentane, 1,6-diaminohexane 1,7-diaminoheptane or similar diaminoalkanes.

Acyl Donors/Amine Acceptors

TGases are capable of linking glutamine-containing peptides and proteins to the ϵ-amino group of a lysine within the structure of a protein if the lysine residue functions as a TGase substrate site. Thus, in accordance with Formula II above, Z represents a peptide or protein containing the Gln residue that is capable of acting as transglutaminase amine acceptor. Peptides shown to crosslink to protein-bound lysine residues via TGase catalysis include: TVQQEL, PGGQQIV, pEAQQIV, PKPOQFM, EAQQIVM, and multiple derivatives of Benzyloxycarbonyl(Cbz)-QG (Grootjans, et al. JBC 270 (39), 22855–22858 (1995)), (Groenen et al. Eur. J. Biochem. 205, 671–674 (1992)), (Gorman et al. JBC 255 (2), 419–427 (1980)). Peptides such as these can be covalently attached to PEG or other polymers, such as those mentioned above, and then attached via TGase catalysis to EPO or other proteins containing amine-donating lysine residues.

Water Soluble Polymers

A particularly preferred water-soluble polymer is one of the several species of PEG. PEG consists of a basic carbon unit, HO—$(CH_2)_2$—OH, and is sold in various forms under the names: Polyethylene glycol (various molecular weights); Poly Ethylene Oxide; Carbowax PEG (various molecular weights); alpha-hydro-omega-hydroxypol y(oxy-1,2-ethanediyl); Ethoxylated 1,2-ethanediol; Polyoxyethylene ether; emkapol 200; gafanol e 200; pluriol e 200; polydiol 200; Polyethylene glycol; PEG; Polyox WSR-301; PEG 200; Macrogol; and Polyoxyethlene. In those aspects of the invention in which PEG-based polymers are used, it is preferred that they have average molecular weights between about 200 and about 100,000 daltons, and preferably between about 2,000 and about 40,000 daltons.

Alternative water-soluble polymeric substances include materials such as dextrans, polyvinyl pyrrolidones, polysaccharides, starches, polyvinyl alcohols, polyacrylamides or other similar non-immunogenic polymers. Those of ordinary skill in the art realize that the foregoing is merely illustrative and unintended to restrict the type of non-antigenic polymers suitable for use herein.

Organic Molecule Imparting Extended Pharmacokinetic Half-Life In Vivo

The organic moieties that can be attached to the hydrophilic polymer to increase the half-life include fatty acids, dicarboxylic acids, monoesters or monoamides of dicarboxylic acids, lipids containing saturated fatty acids, lipids containing unsaturated fatty acids, lipids containing mixtures of saturated and unsaturated fatty acids, simple carbohydrates, complex carbohydrates, carbocycles (such as steroids), heterocycles (such as alkaloids), amino acid chains, proteins, enzymes, enzyme cofactors, or vitamins.

In one embodiment, the hydrophilic polymeric group is substituted with one to about six alkyl, fatty acid, fatty acid ester, lipid or phospholipid groups (as described herein, e.g., Formula I and Formula II). Preferably, the substituted hydrophilic polymeric group is a linear or branched PEG. Preferably, the substituted hydrophilic polymeric group is a linear PEG (e.g., PEG diamine) that is terminally substituted with a fatty acid, fatty acid ester, lipid or phospholipid group or a hydrocarbon. Hydrophilic polymers that are substituted with an alkyl, fatty acid, fatty acid ester, lipid or phospholipid groups group can be prepared using suitable methods. For example, a modifying agent can be prepared by reacting monoprotected PEG diamine with an activated fatty acid (e.g., palmitoyl chloride). The resulting product can be used to produce a modified EPO that comprises a PEG that is substituted with a fatty acid group. A variety of other suitable synthetic schemes can be used. For example, an amine containing polymer can be coupled to a fatty acid or fatty acid ester as described herein, and an activated carboxylate (e.g. activated with N,N'-carbonyl diimidazole) on a fatty acid or fatty acid ester can be coupled to an hydroxyl group on a polymer. In this way, a multitude of suitable linear and branched chain multimeric structures having the desired properties can be constructed and finally linked or modified to contain either a primary amine which will act as the transglutaminase amine donor, or a glutamine-containing peptide or polymer that can act as the transglutaminase amine acceptor.

Fatty acids and fatty acid esters suitable for use in the present invention can be saturated or can contain one or more unsaturated units. In a preferred embodiment, the fatty acids and fatty acid esters comprise from about six to about forty carbon atoms. Fatty acids which are suitable for modifying EPO in the method of the invention include, for example, n-dodecanoate (C12, laurate), n-tetradecanoate (C14, myristate), n-hexadecanoate (C16, palmitate), n-octadecanoate (C18, stearate), n-eicosanoate (C20, arachidate), n-docosanoate (C22, behenate), n-triacontanoate (C30), n-tetracontanoate (C40), cis-D9-octadecanoate (C18, oleate), all cis D5.8.11.14-eicosatetraenoate (C20, arachidonate), octanedioic acid, tetradecanedioic acid, octadecandeioic acid, docosanedioic acid, and the like. Suitable fatty acid esters include monoesters of dicarboxylic acids which comprise a linear or branched lower alkyl group. The lower alkyl group can comprise from one to about twelve, preferably one to about six, carbon atoms. Suitable fatty acid esters for modifying proteins of the invention include, for example, methyl octadecanoate, ethyl octadecanoate, propyl octadecanoate, butyl dodecanoate, sec-butyl dodecanoate, tert-butyl dodecanoate, neopentyl tetradecanoate, hexyl tetradecanoate, methyl cis-Δ9-octadecanoate, and the like.

Preparation of the TGase Substrate for Transfer to Epo

Thus, the artisan can prepare conjugates of two or three parts or more linked to the amine donor amine moiety or to an amine acceptor moiety and the resulting complex will function as the TGase substrate.

The preparation of the other substrates is preferably performed stepwise and in the final step will result in a single deprotected or unprotected primary amine. Thus, if for example, amine-reactive groups including electrophilic groups such as tosylate, mesylate, halo (chloro, bromo, iodo), N-hydroxysuccinimidyl esters (NHS), substituted phenyl esters, acyl halides and the like are to be used to couple water soluble polymer and organic molecules, the primary amine in most cases must be protected. Other methods of conjugating organic molecules to polymers are well known and include the use of agents which can react with thiols, for example, maleimide, iodoacetyl, acrylolyl, pyridyl disulfides, 5-thiol-2-nitrobenzoic acid thiol (TNB-thiol), and the like. Suitable methods to introduce such thiol reactive groups into molecules are known in the art (see for example, Hermanson, G. T., Bioconjugate Techniques, Academic Press: San Diego, Calif. (1996)). An aldehyde or ketone functional group can be coupled to amine-or hydrazide-containing molecules and an azide group can react with a trivalent phosphorous group to form phosphoramidate or phosphorimide linkages. A reactive group can be bonded directly to the hydrophilic polymer, conjugate complex or through a linker moiety, for example a C1–C12 hydrocarbyl group. As used herein, "hydrocarbyl group" refers to a hydrocarbon chain wherein one or more carbon atoms are optionally replaced by a heteroatom such as oxygen, nitrogen or sulfur. Suitable linker moieties include, for example, tetraethylene glycol, $(CH2)_3-$, $-NH-(CH_2)_6-NH-$, $-(CH_2)_2NH-$ and $-CH_2-O-CH_2-CH_2-O-CH_2CH_2-O-CH-NH-$.

Modifying agents which comprise a linker moiety can be produced, for example, by reacting a mono-Boc-alkyl-diamine (e.g. mono-Boc-ethylenediamine, mono-Boc-diaminohexane) with a fatty acid in the presence of 1-ethyl-3-(3-dimethylaminopropyl) carbodiimide (EDC) to form an amide bond between the free amine and the fatty acid carboxylate. The Boc protecting group can be removed from the product by treatment with trifluoroacetic acid (TFA) to expose a primary amine which can be coupled to another carboxylate as described, or can be reacted with maleic anhydride and the resulting product cyclized to produce an activated maleimido derivative of the fatty acid. (See, for example, Thompson, et al., WO 92/16221 the entire teachings of which are incorporated herein by reference).

Examples of derivatized erythropoietic compounds are:

M-PEG-A-EPO where the M-PEG is attached to specific glutamines or lysines using a TGase where M is a lipid, carbohydrate, polysaccharide, fatty acid, fatty acid derivative, fatty alcohol or protein and A is an amine donor, preferably cadaverine or putrescine, or an amine acceptor, preferably a short, glutamine-containing peptide of 1–30 amino acids.

$(M-PEG)_2$-A-EPO where the M-PEG is esterified to two different carboxyl groups on A, where M is a lipid, carbohydrate, polysaccharide, fatty acid, fatty acid derivative, fatty alcohol or protein. Suitable examples of the moiety A having two different carboxyl groups for esterification include diglycerides or triglycerides derivatives as well as derivatives of maleic acid, citraconic acid, glutamic acid or other polymers containing two or more carboxylcarbons. Higher multiples are included as well.

$(M-PEG)_2$-R-A-EPO where the $(M-PEG)_2$—R is two different carboxyl groups on A, where M is a lipid, carbohydrate, polysaccharide, fatty acid, fatty acid derivative, fatty alcohol or protein and R is a valency enhancing construct, such as dendrimers of amino acids and the like, that contain multiple functional groups for the attachment of multiple $(M-PEG)_2$ or other moieties. Higher multiples are included as well.

M-A-EPO where M is a protein or peptide and A is a lysine side chain on said protein or peptide.

M-A-EPO where M is a protein or peptide and A is a glutamine side chain on said protein or peptide.

M-A-EPO where M is a lipid and A is an amine acceptor, preferably a short, glutamine-containing peptide.

M-A-EPO where M is a lipid and A is putrescine, cadaverine or other diaminoalkane.

M-A-EPO where M is biotin, dansyl, or other moiety imparting biophysical characteristics to EPO that are useful for research, diagnostic or therapeutic purposes and A is putrescine, cadaverine, or other suitable TGase amine donor or amine acceptor substrate. In the case where biotin or another moiety having a known binding partner is incorporated into the conjugate, it is anticipated that said conjugate may be used in research, diagnosis or therapy in a complex with its known binding partner such as in a biotin-avidin complex.

Therapeutic Uses

The EPO formulations of the present invention are useful as a parenteral formulation in treating blood disorders characterized by low or defective red blood cell production such as various forms of anemia, including anemia associated with chronic renal failure, zidovidine treated HIV infected patients, and cancer patients on chemotherapy. It may also have application in the treatment of a variety of disease states, disorders and states of hematologic irregularity such as sickle cell disease, beta-thalassemia, cystic fibrosis, pregnancy and menstrual disorders, early anemia of prematurity, spinal cord injury, space flight, acute blood loss, aging and the like. It may also have application in situations where an increase in red blood cells is desired such as in pre-surgery patients. Preferably, the EPO composition of the present invention is administered parenterally (e.g. IV, IM, SC or IP). Effective dosages are expected to vary considerably depending on the condition being treated and the route of administration but are expected to be in the range of 0.1 (~7 U) to 100 (~7000 U) μg/kg body weight of the active material. Preferable doses for treatment of anemic conditions are about 50 to about 300 Units/kg three times a week.

Pharmaceutical Compositions

The erythropoietin glycoprotein products prepared in accordance with this invention may be prepared in pharmaceutical compositions suitable for injection with a pharmaceutically acceptable carrier or vehicle by methods known in the art. For example, appropriate compositions have been described in WO97/09996, WO97/40850, WO98/58660, and WO99/07401. Among the preferred pharmaceutically acceptable carriers for formulating the products of the invention are human serum albumin, human plasma proteins, etc. The compounds of the present invention may be formulated in 10 mM sodium/potassium phosphate buffer at pH 7 containing a tonicity agent, e.g. 132 mM sodium chloride. Optionally the pharmaceutical composition may contain a preservative. The pharmaceutical composition may contain different amounts of erythropoietin products, e.g. 10–2000 µg/ml, e.g. 50 µg or 400 µg.

The stability of the composition can be further enhanced by the addition of antioxidants such as tocopherol, butylated hydroxytoluene, butylated hydroxyanisole, ascorbyl palmitate, or edetates such as e.g. disodium edetate, with the edetates additionally binding possibly present heavy metals. The stability can furthermore be enhanced by the addition of preserving agents such as benzoic acid and parabens, e.g. methylparaben, and/or propylparabene.

Treating Blood Disorders Characterized by Low or Defective Red Blood Cell Production Administration of the erythropoietin glycoprotein products of the present invention results in red blood cell formation in humans. Therefore, administration of the erythropoietin glycoprotein products replenishes this EPO protein that is important in the production of red blood cells. The pharmaceutical compositions containing the erythropoietin glycoprotein products may be formulated at a strength effective for administration by various means to a human patient experiencing blood disorders characterized by low or defective red blood cell production, either alone or as part of a condition or disease. The pharmaceutical compositions may be administered by injection such as by subcutaneous, intravenous or intramuscular injection. Average quantities of the erythropoietin glycoprotein product may vary and in particular should be based upon the recommendations and prescription of a qualified physician. The exact amount of conjugate is a matter of preference subject to such factors as the exact type of condition being treated, the condition of the patient being treated, as well as the other ingredients in the composition. For example, 0.01 to 10 µg per kg body weight, preferably 0.1 to 10 µg per kg body weight, may be administered e.g. once weekly.

Throughout this application, various publications have been referenced. The disclosures in these publications are incorporated herein by reference in order to describe more fully the state of the art.

The present invention is further illustrated by the following examples that are presented for purposes of demonstrating, but not limiting, the preparation of the compounds and compositions of this invention. From initial experiments, at least two, and probably three, of the 7 glutamines on EPO are capable of serving as TGase substrates. Peptide mapping has shown that Gln115 can serve as an acyl donor sight for TGase and that at least one of the other 6 glutamine residues can as well. Attachment of PEG groups and lipid groups containing aliphatic amines to EPO using guinea pig liver TGase was accomplished and it was demonstrated that, following attachment of a 5 kilodalton PEG group, EPO retains about 40% of its activity. Attachment of Cbz-QG, a known acyl donor substrate for TGase, and subsequent peptide mapping, indicate that Lys45 on EPO serves as a very efficient amine donor substrate sight for TGase, and that Lys154 can also serve as an amine donor site.

EXAMPLE 1

Conjugation of Dansyl-Cadaverine Substrate to Human Erythropoietin with Guinea Pig Liver Transglutaminase Recombinant human EPO (rhEPO) (10 uM) was incubated with dansyl-cadaverine (DC) (Sigma, St Louis, Mo.) (3 mM) and TGase (Sigma, St Louis, Mo.) (0.15 U/ml) in 100 mM Tris (pH 7.5) and 10 mM $CaCl_2$ for 3 hours at 37° C. Dansyl-cadaverine is a well known substrate for TGases and provides a fluorescent marker for ease of following the reaction. The reaction mixture was subjected to SDS-PAGE and the results shown in FIG. 2. The fluorescence of the EPO band confirms the attachment of DC via TGase and indicates that amine-acceptor sites exist on EPO. The product was purified on a Zorbax GF-250 XL HPLC column equilibrated with PBS.

The presence of fluorescent dimers and trimers in the gel indicates that EPO can itself act as a TGase substrate by providing a lysine substrate for cross-linking with one or more of the glutamine residues in EPO. The fact that these bands are fluorescent and cross-linked raises the possibility that at least two different glutamine residues on EPO can serve as TGase acyl-donor sites.

EXAMPLE 2

Conjugation of Cadaverine-X-biotin Substrate to Human Erythropoietin with Guinea Pig Liver Transglutaminase Recombinant human EPO (rhEPO) (50–100 uM) is incubated with cadaverine-X-biotin (Biotium, Hayward, Calif.) (30 mM) and TGase (Sigma, St Louis, Mo.) (0.15 U/ml) in 100 mM Tris (pH 7.5) and 10 mM $CaCl_2$ for 3 hours at 37° C. The product is purified on a Zorbax GF-250 XL HPLC column equilibrated with PBS.

EXAMPLE 3

Conjugation of Cbz-QG Substrate to Human Erythropoietin with Guinea Pig Liver Transglutaminase Recombinant human EPO (rhEPO) (1.96 mg/ml) is incubated with N-α-benzyloxycarbonyl glutaminyl glycine (Cbz-QG) (15 mM) (Sigma, St Louis, Mo.) and TGase (Sigma, St Louis, Mo.) (0.15 U/ml) in 100 mM Tris (pH 7.5) and 10 mM $CaCl_2$ for 3 hours at 37° C. The product is purified on a Zorbax GF-250 XL HPLC column equilibrated with PBS.

EXAMPLE 4

Characterization and Peptide Mapping of EPO-DC, EPO-Cadaverine-X-Biotin, and EPO-(Cbz-QG)

Figure 3:
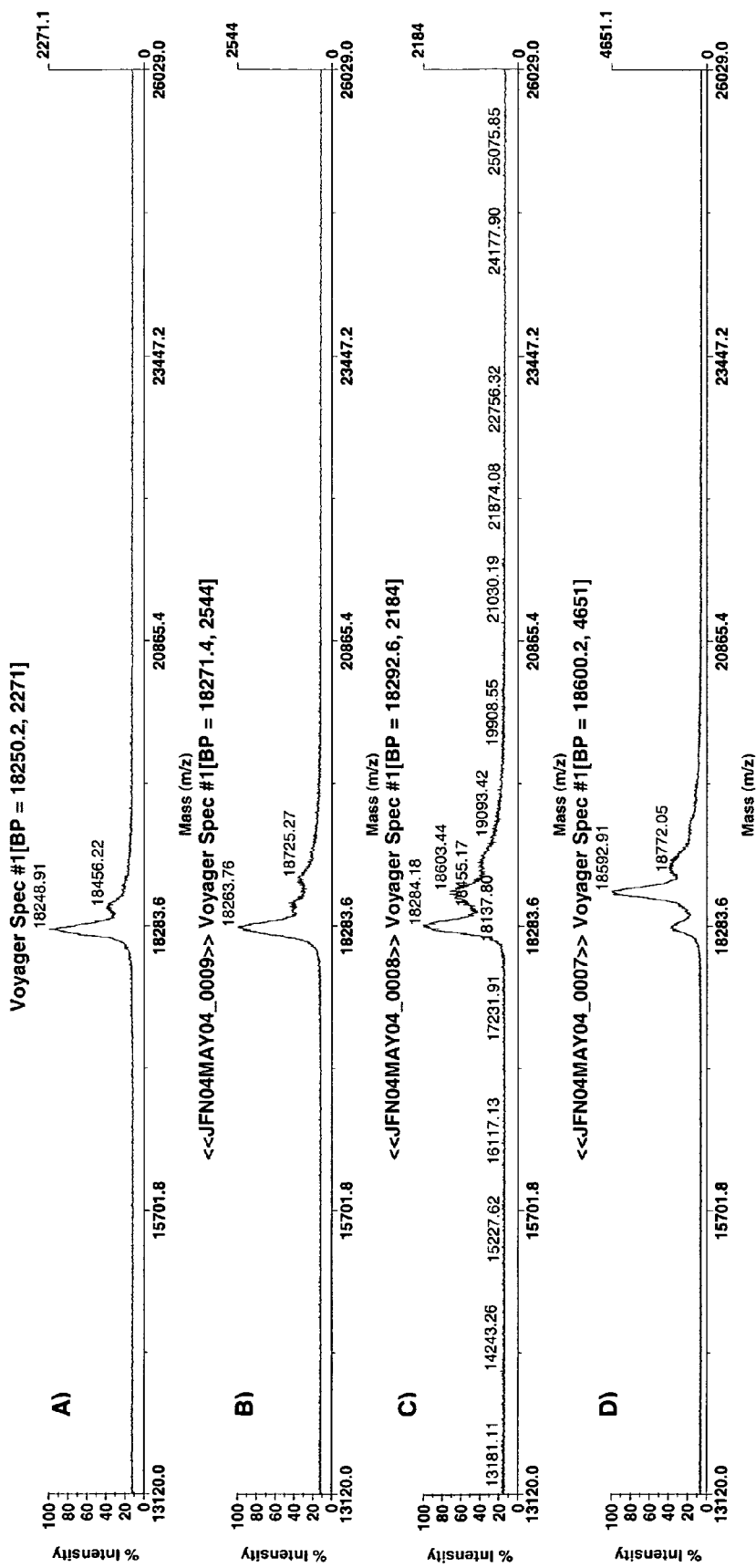
FIG. 3 The MALDI MS analyses of (a) deglycosylated EPO, (b) deglycosylated EPO-cadaverine-X-biotin (should see additions of +424), (c) deglycosylated EPO-DC (should see additions of +318), and (d) deglycosylated EPO-cbz (should see additions of +319).

For deglycosylation, 50 ul of rhEPO or conjugate (0.2–2 mg/ml) was diluted into 50 ul of RapiGest (Waters Corp., Milford, Mass.) (2 mg/ml in PBS). To this was added 10 ul of NP-40 detergent soln (15%), 10 ul each of PNGase F, Sialidase A and O-glycanase (Prozyme, San Leandro, Calif.). The solution was incubated for a total of 96 hrs at 37° C. Intact masses were obtained by mixing the samples with sinapinic acid in 1:1 water/acetomitrile (+0.1% trifriuoroacetic acid) and spotting on a MALDI MS plate, followed by analysis on an ABI Voyager DE-STR MALDI-TOF MS. The proteins were analyzed in linear mode with an acerbating voltage of 25000 V (FIGS. 3 & 5). Following this, 50 µL each, were mixed with 5 µL of 45 mM DTT and the solution incubated at 65° C. for 20 min. Then, 5 µL of 100 mM iodoacetamide was added and the solution was incubated at RT in the dark for 20 mm. Then, 5 µL of Lys-C endoproteinase (Calbiochem, San Diego, Calif.) (1.3 ug/ul) was added and the solutions were incubated at 37° C. for 20–24 h. Each protein digest was separated out using revered-phase HPLC and a Waters Symmetry300 1 ×50 mm C18 column. Each separated digest was automatically spotted on a MALDI plate and analyzed. A saturated mixed matrix of □-cyano-4-hydroxycinnamic acid/dihydroxybenzoic acid (□-cyano/DHB) was used for ionization (FIG. 4).

FIG. 3 shows the intact masses for degylcosylated sample of EPO and each of the conjugates. Panel (B) shows a small peak at 18725 that corresponds to the addition of one cadaverine-X-biotin moiety (calc MW shift=+424). Panel (C) shows a peak at 18603 corresponding to the addition of one dansyl-cadaverine moiety (calc MW shift=+317), and panel (D) shows a peak at 18592 that corresponds to the addition of one Cbz-QG peptide (calc MW shift=+319). From this data, it appears that the attachment of Cbz-QG is more efficient than that of dansyl-cadaverine or cadaverine-X-biotin. In all three cases, however, EPO shows attachment of the TGase substrates.

Figure 4:
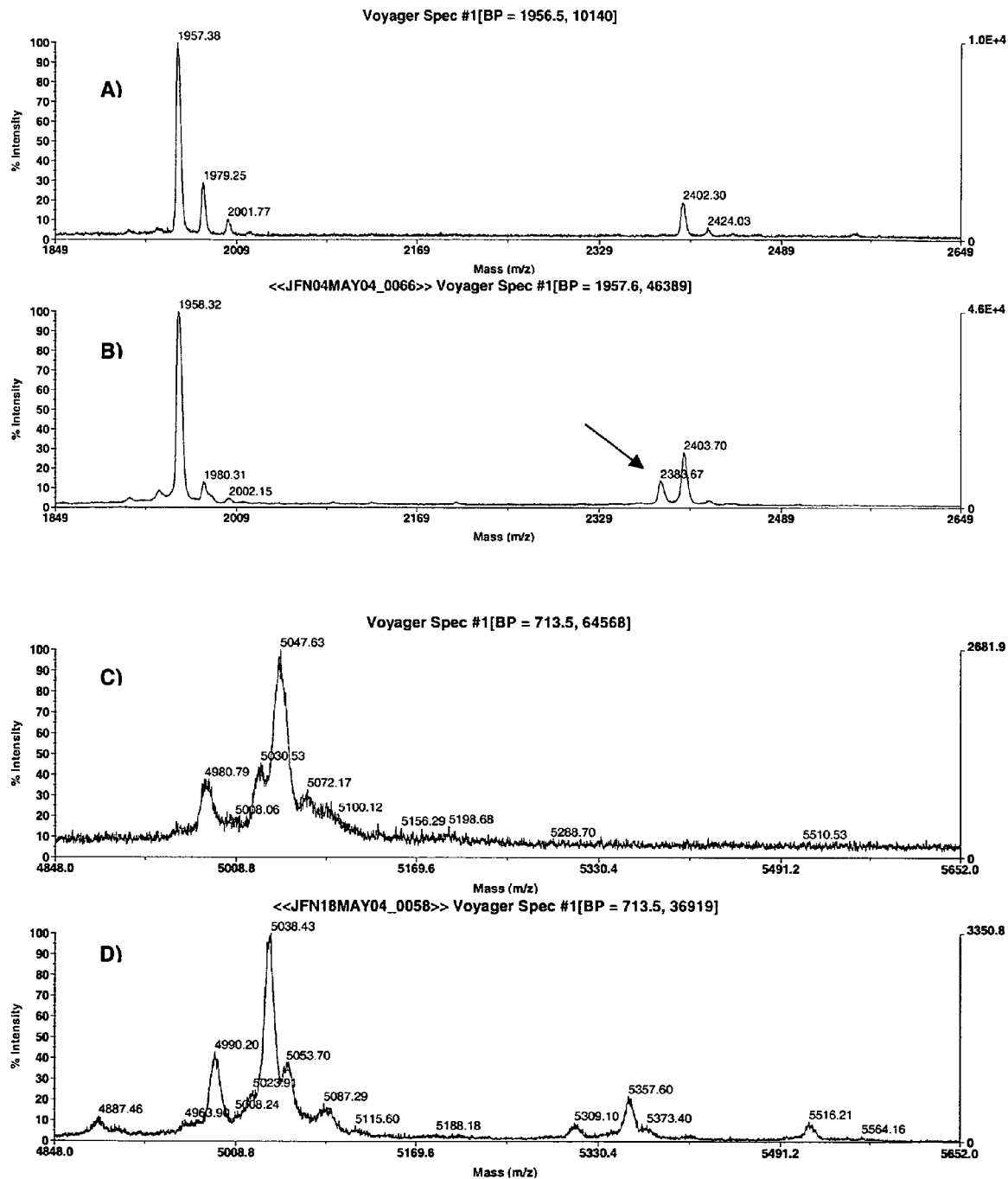
FIG. 4 The MALDI TOF mass spectra for (a) Lys-C digest of EPO (control); (b) Lys-C digest of EPO-X-biotin; (c) Lys-C digest of deglycosylated EPO (control); (d) Lys-C digest of deglycosylated EPO-DC.
Figure 5:
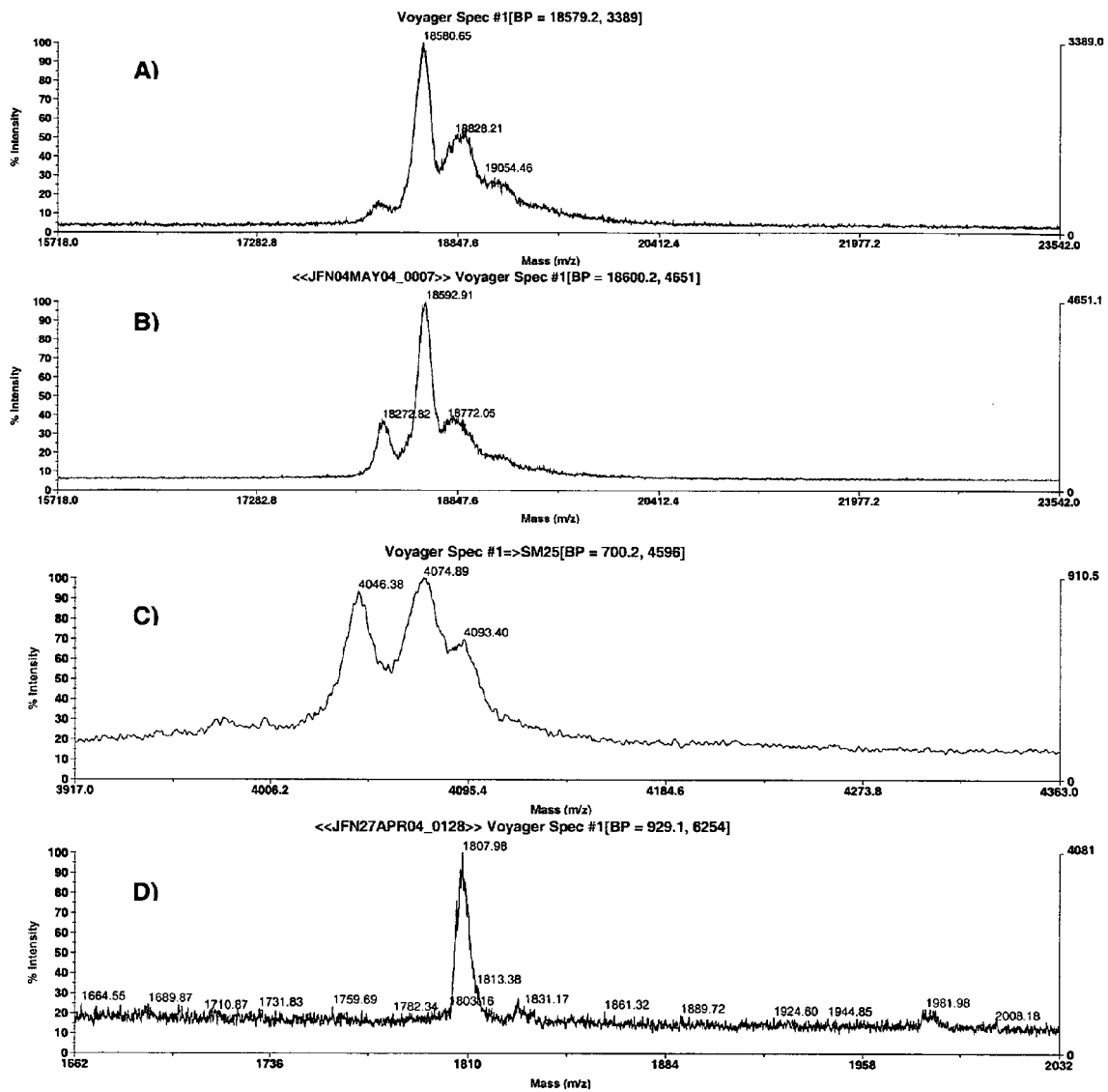
FIG. 5 The MALDI TOF mass spectra for (a) degycosylated EPO-(Cbz-QG) batch #1; (b) deglycosylated EPO-(Cbz-QG) batch #2; (c) Lys-C digest of degycosylated EPO-(Cbz-QG) batch #1; (d) Lys-C digest of degycosylated EPO-(Cbz-QG) batch #1.

FIG. 4 shows mass spectra of the Lys-C digestion of EPO-cadaverine-X-biotin and EPO-DC. The peak at 1958 in panels (A) and (B) corresponds to that containing residues 98–116 of EPO. The peak indicated by the arrow corresponds to the addition of cadaverine-X-biotin to that peptide. This indicates that Gln115 serves as a TGase substrate site since it is the only Gln residue in that peptide and TGase will only attach cadaverine to Gln residues. Panels (C) and (D) of FIG. 4 show MALDI MS of the Lys-C digests of deglycosylated EPO and EPO-DC. The peak around 5038 corresponds to residues 53–97 (calc MW=5024.8) of EPO. In panel (D), the peak at 5357 corresponds to a molecular weight shift of 319 indicating that a dansyl cadaverine moiety has been attached at a residue within this region of the protein. Since 6 glutamines are contained in this peptide, the identity of the modified residue could not be ascertained.

Panels (A) and (B) of FIG. 5 show MALDI TOF mass spectra of two different batches of deglycosylated rhEPO-(Cbz-QG). The peak around 18580 corresponds to the attachment of one Cbz-QG (calc MW shift=+319) moiety to rhEPO and both spectra indicate that a majority of the protein is modified in both batches and that the attachment of this peptide to rhEPO is very reproducible. Panels (C) and (D) show MALDI TOF mass spectra of the Lys-C digest of deglycosylated rhEPO-(Cbz-QG). Panel (C) shows a peak at 4046 corresponding to residues 21–52 of EPO with an additional Cbz-QG moiety at Lys45 (calculated MW=4032.1). The Lys-C did not cleave at Lys45 due to the modification. Panel (D) shows a peak at 1807 corresponding to residues 153–165 with an additional Cbz-QG moiety (calculated MW=1802.6). In this peptide, Lys154 was not cleaved due to the attachment of the Cbz-QG indicating that Lys154 is modified.

A large mass window was necessary for obtaining the MALDI TOF mass spectra described here. Due to this, significant drift was observed in the spectra. For this reason, the molecular weight changes for the conjugates were calculated by comparing to the molecular weight observed for unmodified EPO in each individual sample. Taken together, the mass data for the intact, deglycosylated samples and the Lys-C digestion data, confirm that Gln 115 was modified with both cadaverine-X-biotin, and dansyl-cadaverine, and that at least one other Gln residue in rhEPO received a dansyl-cadaverine modification in the presence of TGase. The data also show that Lys45 and Lys154 of rhEPO received a Cbz-QG modification in the presence of TGase and that in both batches analyzed, up to 90% of the protein was modified.

EXAMPLE 5

UT7 Assay of rhEPO-(Cbz-QG)

Figure 6:
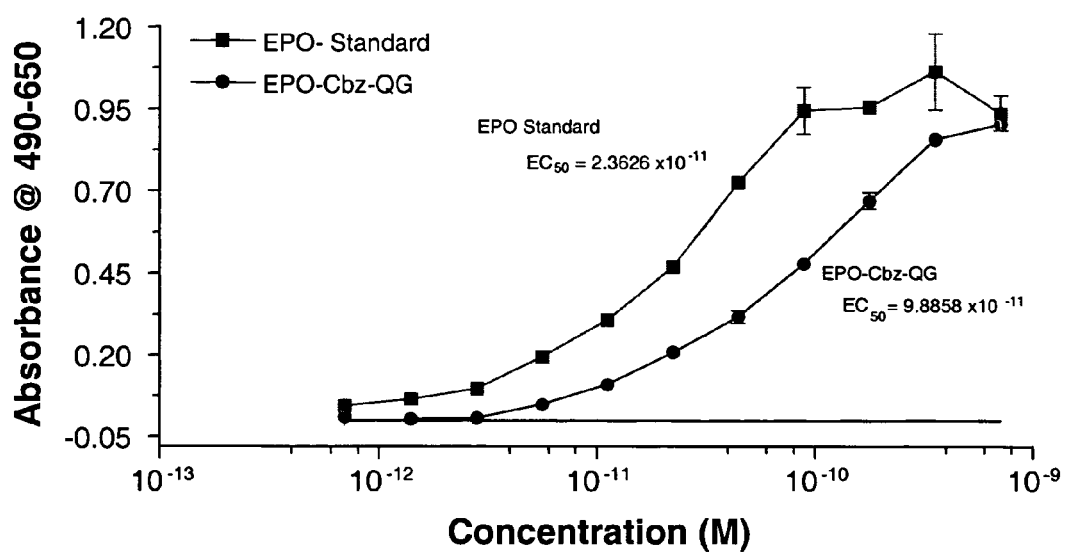
FIG. 6 shows a graph of the absorbance vs. concentration of added EPO species for the hematopoiesis of UT7 cells incubated with EPO-(Cbz-QG) or unmodified EPO (EPO-control).

A UT7 assay was performed on the rhEPO-(Cbz-QG) as follows: UT7 cells were starved in IMDM with L-glu and 5% FBS without Epo for 24 hrs prior to assay. Cells were washed and plated at 30,000 cells per well. Dilutions of EPO (20–0.01952 ng/mL) and rhEPO-(Cbz-QG) (20–0.01952 ng/mL) were added and assayed in duplicate. The plate was incubated for 48 hrs at 37° C. and assayed with Promega's MTS solution with OD readings taken at 1, 2 and 3 hr intervals. Values were background corrected with SoftMax Pro. Average background was 0.292. The assay shows that the conjugate is approximately 4-fold less active than unmodified EPO (see FIG. 6) indicating that the modification did not occur at a residue involved significantly in receptor binding. This implies that modification of Lys45 or Lys154 does not contribute to a significant loss in activity and suggests that other modifications or mutations could be made at these sites without significantly effecting the ability of rhEPO to bind to its receptor.

EXAMPLE 6

Synthesis of Cadaverine-PEG(20K)

Cadaverine-PEG(20K) was synthesized using commercially available reagents. 25 mg of cadaverine hydrochloride salt (Sigma, St. Louis, Mo.) was dissolved in 5 ml of PBS and pH was adjusted to 7. To this was added 25 mg of mPEG(20K)-Succinimidyll propionate (Shearwater Corp., Huntsville, Ala.) and the reaction was incubated at 22° C. for 2 hours. The reaction mixture was dialyzed against 0.1% acetic acid in water and lyophilized.

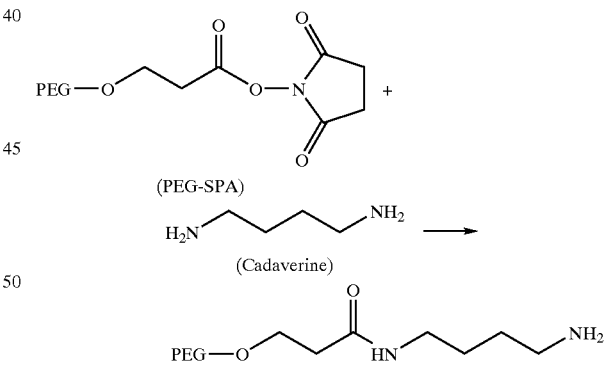

EXAMPLE 7

Synthesis of Putrescine-PEG(20K)

Putrescine-PEG(5K) was synthesized by dissolving 300 mg putrescine hydrochloride (Sigma, St. Louis, Mo.) in 10 ml of PBS and adjusting pH to 7. 100 mg of mPEG(5K)-Succinimidyll propionate (Shearwater Corp., Huntsville, Ala.) was added and allowed to react for two hours at 22° C. The reaction mixture was dialyzed against 0.1% acetic acid in water and lyophilized.

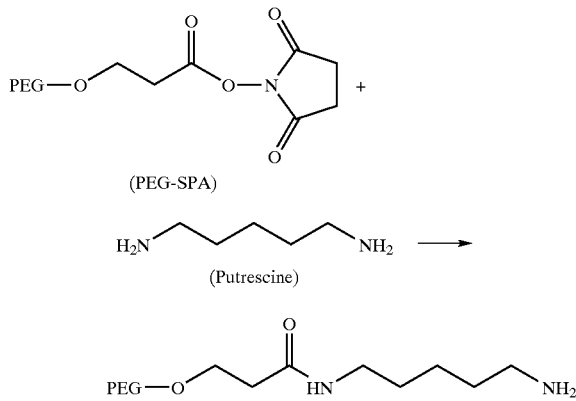

(PEG-SPA)

(Putrescine)

EXAMPLE 8

Synthesis of Putrescine-PEG-DSPE(3.4K)

Putrescine-PEG-DSPE(3.4K) was synthesized by dissolving 176.5 mg of putrescine in 1.765 ml of PBS (ph 7.4). 13.5 mg of NHS-PEG-DSPE(3.4K) (Shearwater Corp., Huntsville, Ala.) was dissolved in 1 ml of ethanol/PBS (1:1). 1 ml of the NHS-PEG-DSPE solution was then added dropwise to 1.704 ml of the putrescine solution and the reaction was stirred at 22° C. for 4 hours and then purified on a Zorbax GF-250 XL column equilibrated with 0.1% acetic acid (pH 4.5).

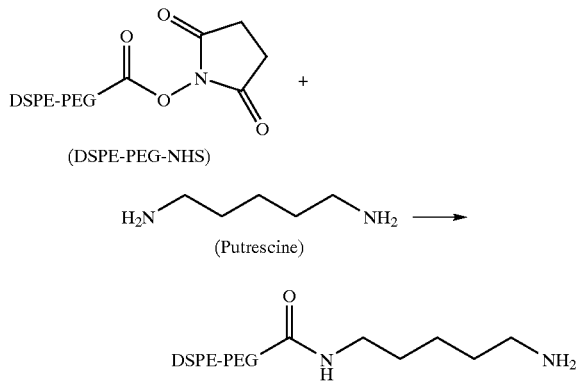

(DSPE-PEG-NHS)

(Putrescine)

EXAMPLE 7

Figure 7:
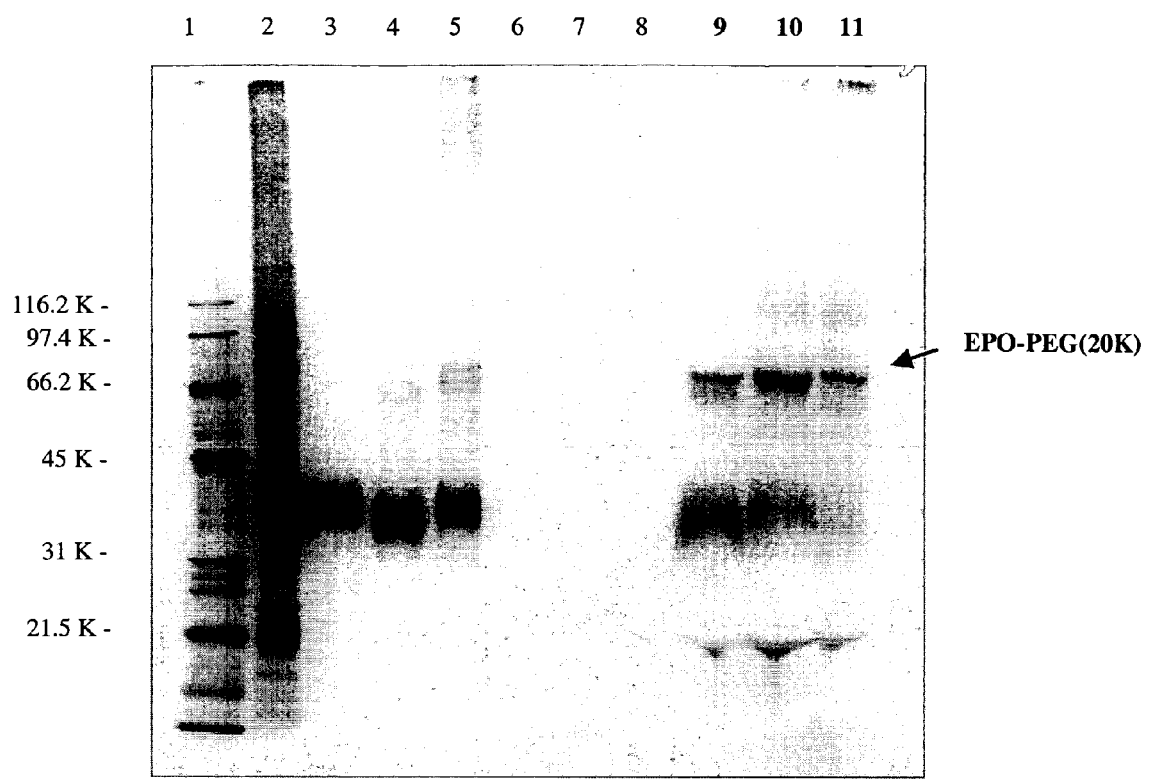
FIG. 7 is an image of a silver-stained polyacrylamide gel showing the attachment of cadaverine-PEG(20K) to EPO via TGase catalysis: Lane 1=molecular weight markers. Lane 2=EPO+TGase+DC. Lane 3=EPO standard. Lane 4=EPO+TGase (6 hrs); Lane 5=EPO+TGase (22 hrs); Lanes 6 and 7=TGase (6 hrs and 22 hrs resp.); Lane 8=PEG(20K)-cadaverine; Lanes 9, 10 and 11=EPO+PEG20K-cadaverine+TGase (6 hrs, 22 hrs, and 22 hrs (reduced), resp.). Note that the EPO+DC sample was overloaded such that the fluorescent signal of the DC could be maximized.
Figure 8:
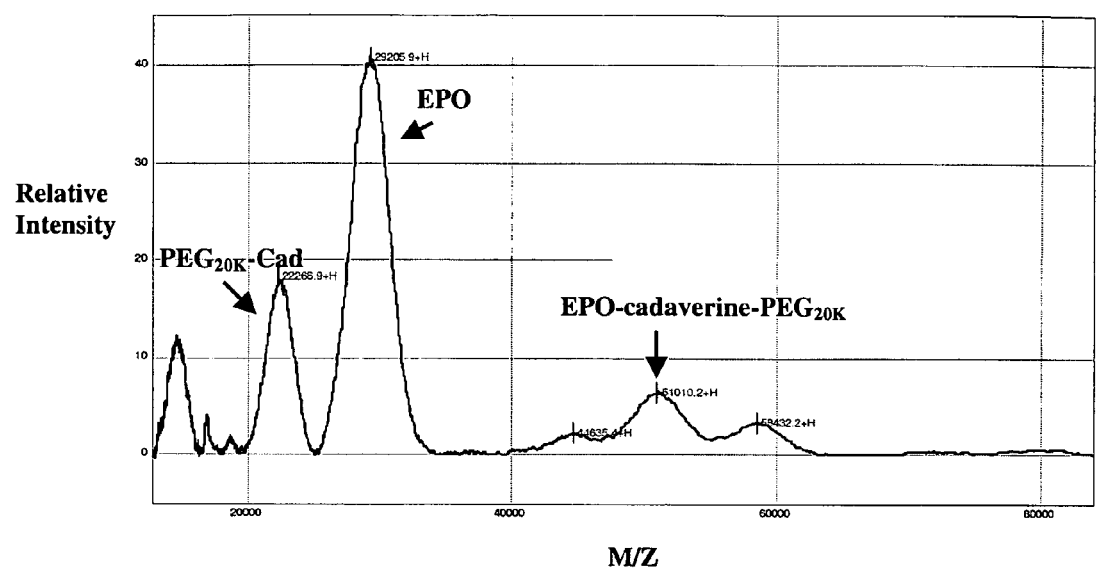
FIG. 8 shows a tracing of the intensity vs. mass to charge ratio in a SELDI-MS of the reaction mixture of EPO+PEG20K-cadaverine+TGase. The peak at 51,010 corresponds to the PEGylated EPO product.

Conjugation of Cadaverine-PEG(20K) Substrate to Human Erythropoietin with Guinea Pig Liver Transglutaminase Cadaverine-PEG(20K) was reacted with EPO using the conditions given in Example 1 except that 3.3 mM cadaverine-PEG(20K) was used in place of DC. FIG. 7 shows the SDS-PAGE gel of the reaction products and FIG. 8 shows the SELDI mass spec of the products. Both indicate that the cadaverine-PEG(20K) was attached to EPO. Samples for SELDI-MS were prepared by desalting with C-4 zip tips (from Millipore) and spotting on gold SELDI chips using standard protocols.

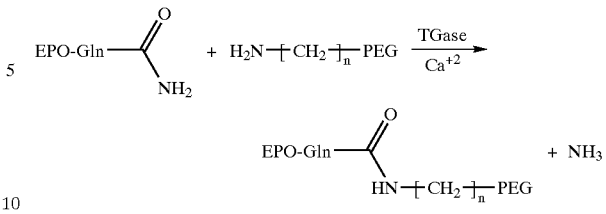

EXAMPLE 8

Figure 9:
FIG. 9 shows a silver-stained SDS-PAGE gel (4–20%) of EPO (lane 1) and purified EPO-PEG5K-putrescine (lane 2). Note that very little unmodified EPO is present in the EPO-putrescine-PEG5K sample.
Figure 10:
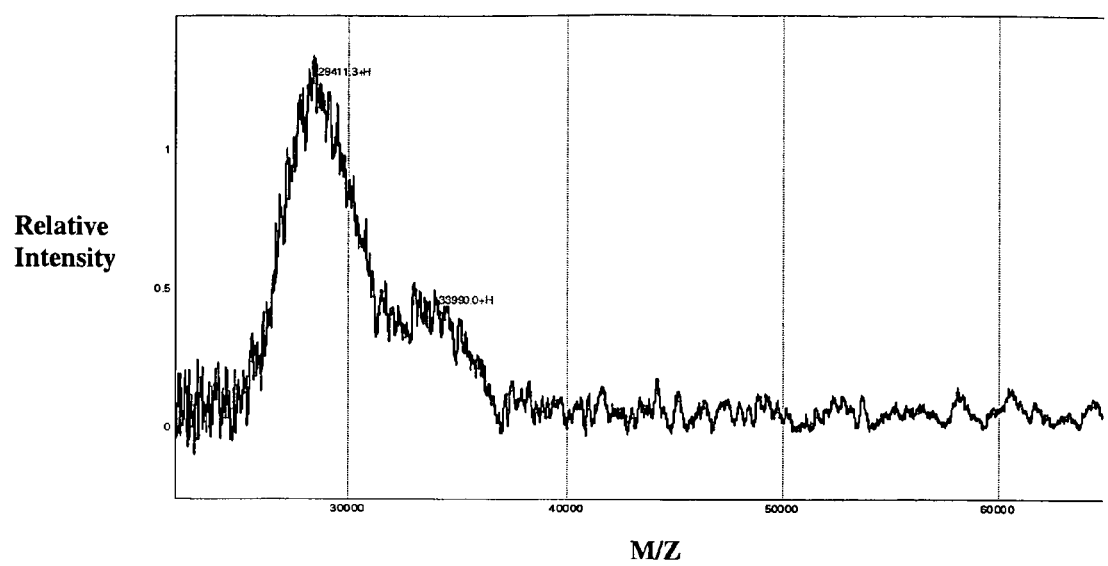
FIG. 10 shows a tracing of the intensity vs. mass to charge ratio in a SELDI-MS of the reaction mixture (EPO+PEG (5K)-putrescine+TGase).
Figure 11:
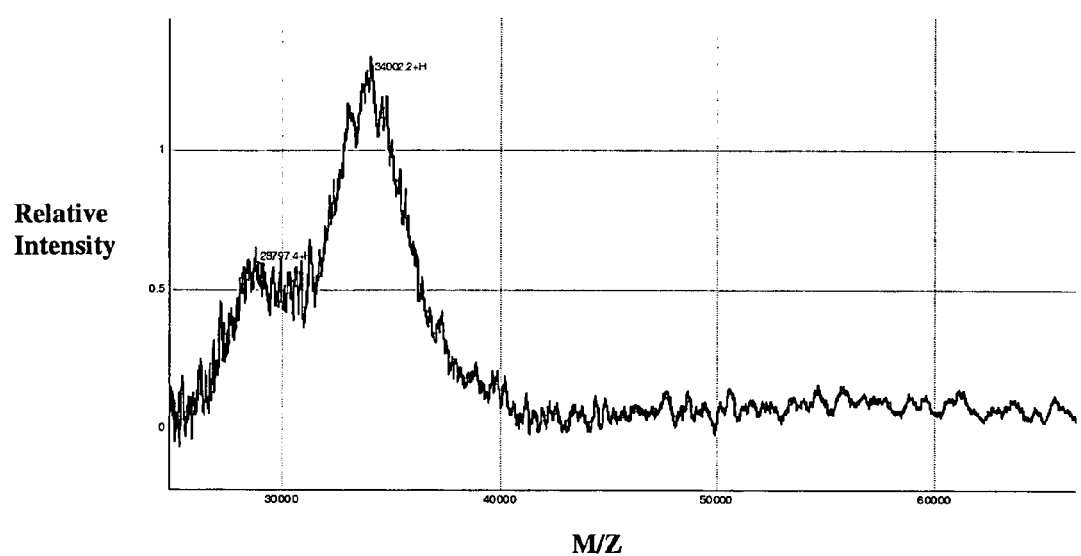
FIG. 11 shows a tracing of the intensity vs. mass to charge ratio in a SELDI-MS for the purified EPO-PEG(5K)-putrescine. (Note that the PEG group tends to suppress ionization and thus the peak areas are not indicative of the relative amount of each species present.)
Figure 12:
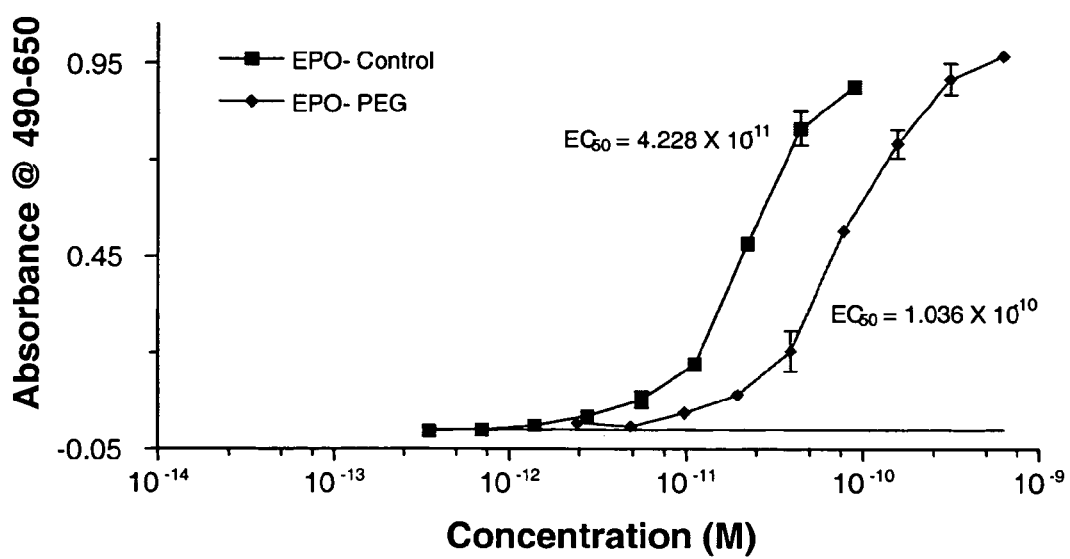
FIG. 12 shows a graph of the absorbance vs. concentration of added EPO species for the hematopoiesis of UT7 cells incubated with EPO-putrescine-PEG(5K) (EPO-PEG) or unmodified EPO (EPO-control).

Conjugation of Putrescine-PEG(5K) Substrate to Human Erythropoietin with Guinea Pig Liver Transglutaminase Putrescine-PEG(5K) was reacted with EPO using the conditions described in example 7 except that 5 mM PEG (5K)-putrescine was used in place of PEG(20K)-cadaverine. Putrescine is known to be a better substrate for TGases than cadaverine (Folk and Chung, 1973 supra). FIG. 9 shows the SDS-PAGE gel (4–20%) of the purified EPO-putrescine-PEG(5K) compared with the EPO stock, FIG. 10 shows the SELDI-MS of the reaction mixture consisting of EPO+TGase+putrescine-PEG(5K), and FIG. 11 shows the SELDI-MS of the purified EPO-putrescine-PEG(5K). These data indicate that the putrescine-PEG(5K) was successfully conjugated to EPO and that the purified EPO-putrescine-PEG(5K) contains only a small amount of unmodified EPO. SELDI samples were prepared by spotting on H-4 SELDI chips, washing with 3 ul of water and adding 1 ul of saturated sinnapinnic acid. A UT7 assay was performed on the EPO-putrescine-PEG(5K) as follows: UT7 cells were starved in IMDM with L-glu and 5% FBS without Epo for 24 hrs prior to assay. Cells were washed and plated at 30,000 cells per well. Dilutions of EPO (2.5–0.0025 ng/mL) and EPO-PEG (20–0.01952 ng/mL) were added and assayed in duplicate. The plate was incubated for 48 hrs at 37° C. and assayed with Promega's MTS solution with OD readings taken at 1, 2 and 3 hr intervals. Values were background corrected with SoftMax Pro. Average background was 0.293. The assay shows that the conjugate is approximately 2.5-fold less active than unmodified EPO (see FIG. 12) indicating that the modification did not occur at a residue involved significantly in receptor binding. Most likely, the loss in activity is due to the PEG interfering sterically at the binding interface.

EXAMPLE 9

Figure 13:
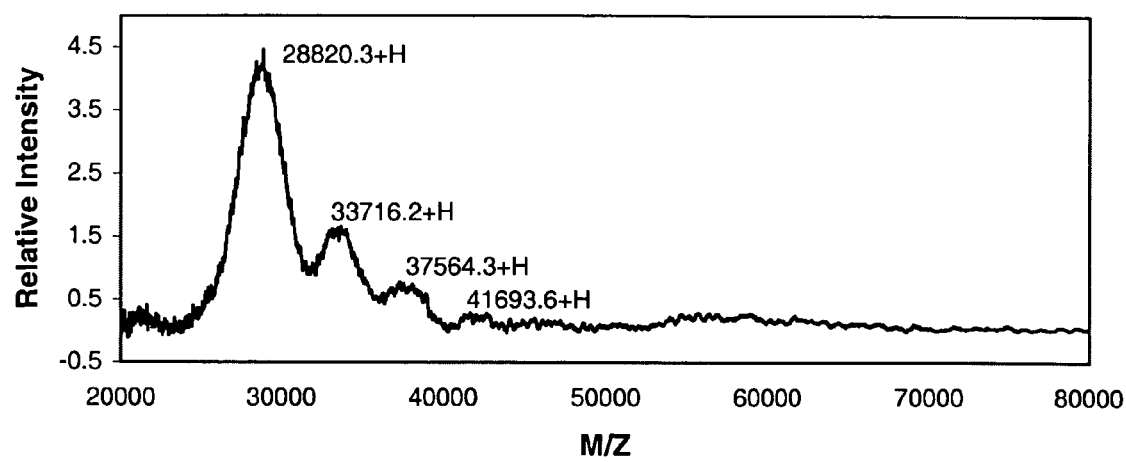
FIG. 13 shows a tracing of the intensity vs. mass to charge ratio in a SELDI-MS of the reaction of EPO+putrescine-PEG-DSPE3.4K+TGase (55% ethanol and 45% TGase reaction buffer, pH 7.5). The peak at 28.8K corresponds to unmodified EPO, while the peaks at 33.7K, 37.5K and 41.6K correspond to the addition of one, two and three putrescine-PEG-DSPE3.4K moieties per EPO. (Note that the lipid group tends to suppress ionization and thus the peak areas are not indicative of the relative amount of each species present.)

Conjugation of Putrescine-PEG-DSPE(3.4K) Substrate to Human Erythropoietin with Guinea Pig Liver Transglutaminase Putrescine-PEG-DSPE(3.4K) (5.1 mM) was incubated with EPO (4.8 uM) in varying concentrations of ethanol (up to 55%) and TGase (0.15 U/ml) in 100 mM Tris (pH 7.5) and 10 mM $CaCl_2$. SELDI-MS indicates that at 55% ethanol, up to 3 putrescine-PEG-DSPE(3.4K) moieties were attached per EPO (see FIG. 13), although the reaction volumes were not sufficient to quantitate the percent of EPO modified. These data also confirm that up to three glutamine residues on EPO can serve as TGase substrates under these conditions. SELDI samples were prepared by spotting on H-4 SELDI chips, washing with 3 ul of water and adding 1 ul of saturated sinnapinnic acid.

These examples show that at least 3 glutamine residues on EPO can serve as sites for attachment of small molecules, PEG groups (from 5K-20K), PEGylated lipids, and proteins via TGase catalysis. The bioactivity of one PEGylated construct was confirmed, and was shown to be only slightly reduced. If the circulation half-life is significantly improved due to any of these modifications, such a small loss of activity could be insignificant when compared to the potentially improved pharmacokinetics of the modified protein.

EXAMPLE 10

Synthesis of TGase Amine Acceptor Substrates and Attachment to rhEPO

Peptides containing at least one glutamine residue are synthesized by standard solid phase Fmoc chemistry. Following completion of the synthesis, the peptide resin is deprotected with piperidine, washed, and reacted with PEG or other polymer containing an activated ester. Following reaction, the peptide-PEG conjugate is cleaved from the resin using standard TFA conditions and precipitated in ether. The peptide-PEG conjugate is then purified by reversed phase HPLC and lyophylized.

Recombinant human EPO (rhEPO) (10 uM) is incubated with peptide-PEG conjugate (15 mM) and TGase (Sigma, St Louis, Mo.) (0.15 U/ml) in 100 mM Tris (pH 7.5) and 10 mM $CaCl_2$ for 3 hours at 37° C. The reaction mixture is subjected to SDS-PAGE and the product is purified on a Zorbax GF-250 XL HPLC column equilibrated with PBS.

EXAMPLE 11

UT7 Cell Proliferation Assay

UT7 is a human leukemic cell line that has been adapted to become EPO dependant (Komatsu, N., et al. Blood 82(2), 456–464, 1993). The UT7 cells are washed three times in PBS and starved for EPO for 24 hours prior to assay. UT-7 cells were starved in IMDM media with added L-glutamine and FBS at 5% (I5Q). Cells are washed once in 50 mL DPBS and counted while suspended in DPBS and suspended in the appropriate media to a final concentration of $6\times10^5$ cells/mL (yields a final concentration of 30,000 cells per well). An EPO standard is prepared by diluting EPO stock (1.7 mg/mL) to 0.851 g/mL (2 $\mu$L in 4 mL media). The stock solution is diluted 2:340 to 5 ng/mL followed by 1:2 serial dilutions down to a concentration of 0.0098 ng/mL in I5Q media. The resulting dilutions provides standards at concentrations of 2.5 ng/mL to 0.0024 ng/mL. The test sample is diluted in a similar manner. A 50 $\mu$L aliquot of the UT-7 cell suspension is transferred to the corresponding wells and the plates were incubated at 37° C. for 48 hours. Cell proliferation is assessed using Promega's MTS solution, adding 20 $\mu$L per well. Readings begin 1 hour after MTS addition.

What is claimed is:

1. An erythropoietic conjugate having the biological properties of causing bone marrow cells to increase production of reticulocytes and red blood cells, comprising a moiety of the formula:

$$EPO\text{-}[Gln\text{-}A\text{-}X\text{-}(M)_n]_y$$

where EPO is erythropoietin or its pharmaceutical acceptable derivatives having biological properties of causing bone marrow cells to increase production of reticulocytes and red blood cells; Gln is a glutamine residue selected from one or more glutamine residues within the primary sequence of EPO; y is an integer from 1 to 7 indicating the number of modified glutamine residues; A is an amine donor moiety, wherein the linkage between the glutamine residue and the amine donor moiety is of the formula —$CH_2$—CO—NH— where the gamma carboxamide group of the peptide bound glutamine residue is the acyl donor and the —NH-moiety is from the amine donor; X is an optional hydrophilic polymer moiety; M is an optional organic molecule characterized in that it is capable of increasing the circulating half-life of the EPO molecule; and n is an integer from 0 to 15, and the pharmaceutically acceptable salts or esters thereof.

2. The erythropoietic conjugates of claim 1 that cause bone marrow cells to increase production of red blood cells, and said increase is sustained after administration of said erythropoietin conjugate for a greater period of time than that seen after administration of unconjugated erythropoietin.

3. The erythropoietic conjugate of claim 2, where the sustained effect is due to increased serum half life over unmodified mammalian erythropoietin.

4. The erythropoietic conjugate of claim 1 wherein M is one to about six organic moieties, which are each independently selected from a fatty acid group, a fatty acid ester group, a lipid or a phospholipid.

5. The erythropoietin conjugate of claim 1 wherein the hydrophilic polymer is a polyalkylene oxide.

6. The erythropoietic conjugate of claim 1, wherein said erythropoietin or erythropoietic moiety is selected from recombinant and non-recombinant mammalian erythropoietin.

7. The erythropoietic conjugate of claim 5, wherein the polyalkylene oxide is a substituted polyethylene oxide.

8. The erythropoietic conjugate of claim 5, wherein the polyalkylene oxide is selected from polyethylene glycol homopolymers, polypropylene glycol homopolymers, alkylpolyethylene oxides, bispolyethylene oxides and co-polymers or block co-polymers of polyalkyene oxides.

9. The erythropoietic conjugate of claim 1 wherein said hydrophilic polymer is bonded to from one to seven of GLN 58, GLN 59, GLN65, GLN78, GLN 86, GLN92, GLN115 of the mature chain EPO.

10. The erythropoietic conjugate of claim 5, wherein said polyalkylene oxide is a polyethylene glycol homopolymer having a molecular weight of between about 200 and about 100,000 Daltons.

11. The erythropoietic conjugate of claim 1 wherein said hydrophilic polymeric group is a linear or branched polyalkane glycol chain, a carbohydrate chain, an amino acid chain or a polyvinyl pyrrolidone chain, and wherein said hydrophilic polymeric group has a molecular weight of about 800 to about 120,000 Daltons.

12. The erythropoietic conjugate of claim 11 wherein said hydrophobic polymeric group is a linear or branched polyalkane glycol chain with a molecular weight greater than 2,000 Daltons.

13. The erythropoietic conjugate of claim 11 wherein said hydrophilic polymeric group is a linear or branched polyethylene glycol chain or a linear or branched substituted polyethylene glycol chain, n is an integer other than O and the organic moiety is selected from an alkyl group, a $C_6$–$_{40}$ fatty acid group, a $C_6$–$_{40}$ fatty acid ester group, a lipid group and a phospholipid group.

14. The erythropoietic conjugate of claim 11 wherein said hydrophilic polymeric group is a linear or branched polyethylene glycol chain that is terminally substituted with an organic moiety selected from an allkyl group, a $C_6$–$_{40}$ fatty acid group, a $C_6$–$_{40}$ fatty acid ester group, a lipid group or a phospholipid group.

15. The erythropoietic conjugate of claim 13 wherein said organic moiety is palmitoyl.

16. The erythropoietic conjugate of claim 13 wherein the organic moiety is disteroylphosphatidyl ethanolamine (DSPE).

17. The erythropoetic conjugate of claim 13 wherein the hydrophilic polymer-organic moiety is covalently bonded to from one to seven of GLN 58, GLN59, GLN65, GLN78, GLN 86, GLN92, GLN 115 of the mature chain EPO.

18. The conjugate of claim 1 where A is an amine donor transglutaminase substrate, X is PEG or other water soluble polymer and is optional, and M is a biotin, dansyl, or other organic moiety imparting biophysical characteristics to EPO that are useful for research, diagnostic or therapeutic purposes.

19. A method of preparing an EPO conjugate having erythropoietic activity of the formula:

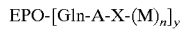

EPO-[Gln-A-X-(M)$_n$]$_y$ where EPO is erythropoietin or its pharmaceutical acceptable derivatives having biological properties of causing bone marrow cells to increase production of reticulocytes and red blood cells; Gln is a glutamine residue selected from one or more glutamine residues within the primary sequence of EPO; y is an integer from 1 to 7 indicating the number of modified glutamine residues; A is an amine donor moiety, wherein the linkage between the glutamine residue and the amine donor moiety is of the formula —$CH_2$—CO—NH— where the gamma carboxamide group of the peptide bound glutamine residue is the acyl donor and the —NH-moiety is from the amine donor; X is a hydrophilic polymer moiety; M is an organic molecule characterized in that it has the capability of increasing the circulating half-life of the EPO molecule; and n is an integer from 0 to 15, and the pharmaceutically acceptable salts or esters thereof;
comprising contacting an erythropoetic or an erytliropoetic protein having a water accessible glutamine residue with a preconstructed hydrophilic polymer-organic moiety complex of the formula A-X(M)$_n$, capable of acting as a transglutaminase substrate in the presence of transglutaminase under conditions such that an EPO-polymer-organic moiety conjugate is formed.

20. The method of claim 19, wherein said polymer is a polyalkylene oxide.

21. The method of claim 20, wherein said polyalkylene oxide is an alpha-substituted polyalkylene oxide.

22. The method of claim 21, wherein said polyalkylene oxide is a polyethylene glycol.

23. The method of claim 19, wherein the transglutaminase is a mammalian protein.

24. The method of claim 19, wherein the transglutaminase is a bacterial protein.

25. The method of claim 19, wherein the transglutaminase is a prokaryotic protein.

26. The method of claim 19 where A is an amine donor transglutaminase (TGase) substrate, X is PEG or other water soluble polymer, and M is biotin, dansyl, or other moiety imparting biophysical characteristics to EPO that are useful for research, diagnostic or therapeutic purposes.

27. A method of treating anemia comprising administering a therapeutically effective amount of conjugate of claim 1.

28. The method of claim 27 wherein said conjugate is characterized by increased serum half-life-compared to the unconjugated erythropoietin.

29. An erythropoietic protein or protein conjugate containing recombinant or non-recombinant mammalian erythropoietin in which any or all of the residues GLN 58, GLN59, GLN65, GLN78, GLN86, GLN92 and GLN115 have been modified by recombinant, enzymatic or chemical means to modify the TGase substrate properties and thereby increase the circulation half life or otherwise alter the biological activity of said erythropoietic protein.

30. An erythropoietic protein or protein conjugate of claim 29 wherein one or more of said glutamine residues are chemically modified, eliminated or changed to another amino acid such that the ability of the glutamine residue to act as a TGase substrate is increased, decreased or eliminated.

31. The erythropoietin conjugate of claim 1 wherein the amine donor A contains a second functional group that allows for the conjugation by chemical means of the polymer X and/or the organic moiety M to said second functional group.

32. The erythropoietin conjugate of claim 31 wherein the second functional group is a thiol, aldehyde, hydrazide, maleimide or cysteine group.

* * * * *